(12) United States Patent
Lou et al.

(10) Patent No.: US 10,945,736 B2
(45) Date of Patent: Mar. 16, 2021

(54) FIXING DEVICE FOR BLOOD VESSEL SUTURING

(71) Applicant: INDUSTRIAL TECHNOLOGY RESEARCH INSTITUTE, Hsinchu (TW)

(72) Inventors: Wan-Shiun Lou, Taichung (TW); Yuen-Yung Loh, Taoyuan (TW); Yung-Lung Liu, Taichung (TW); Wei-Lin Yu, Zhubei (TW); Yen-Ling Wang, Kaohsiung (TW); Hsin-Hsin Shen, Zhudong Township (TW); Chia-Hao Chang, Zhudong Township (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 196 days.

(21) Appl. No.: 16/225,714

(22) Filed: Dec. 19, 2018

(65) Prior Publication Data
US 2020/0178966 A1 Jun. 11, 2020

(30) Foreign Application Priority Data

Dec. 6, 2018 (TW) .................................. 107143900

(51) Int. Cl.
*A61B 17/11* (2006.01)
*A61B 17/04* (2006.01)
(Continued)

(52) U.S. Cl.
CPC .......... *A61B 17/11* (2013.01); *A61B 17/0482* (2013.01); *A61B 17/1227* (2013.01);
(Continued)

(58) Field of Classification Search
CPC ..... A61B 17/04; A61B 17/0482; A61B 17/11; A61B 17/1227; A61B 17/122;
(Continued)

(56) References Cited

U.S. PATENT DOCUMENTS

| 3,561,448 A | 2/1971 | Peternel |
| 3,911,926 A | 10/1975 | Peters |

(Continued)

FOREIGN PATENT DOCUMENTS

| CN | 1292665 A | 4/2001 |
| CN | 101902975 A | 12/2010 |

(Continued)

*Primary Examiner* — Katherine M Shi
*Assistant Examiner* — Alyssa M Keane
(74) *Attorney, Agent, or Firm* — Birch, Stewart, Kolasch & Birch, LLP

(57) ABSTRACT

A fixing device for suturing of blood vessels is provided, which includes a connecting rod, a first clamping member, a second clamping member, a first extension tube and a second extension tube. One end of the first clamping member is disposed on the connecting rod, and the other end of the first clamping member has a first clamping head. One end of the second clamping member is disposed on the connecting rod, and the other end of the second clamping member has a second clamping head. The first extension tube is disposed on an inner side of the first clamping head. The second extension tube is disposed on an inner side of the second clamping head and opposite to the first extension tube, wherein a relative position of the first extension tube and the second extension tube is adjustable.

14 Claims, 7 Drawing Sheets

(51) Int. Cl.
*A61B 17/122* (2006.01)
*A61B 17/12* (2006.01)

(52) U.S. Cl.
CPC ............... *A61B 2017/1103* (2013.01); *A61B 2017/1107* (2013.01); *A61B 2017/1132* (2013.01); *A61B 2017/12004* (2013.01)

(58) Field of Classification Search
CPC ............... A61B 17/08; A61B 17/083; A61B 2017/00858; A61B 2017/1103; A61B 2017/1107; A61B 2017/1132; A61B 2017/12004
USPC ........................................................ 606/150
See application file for complete search history.

(56) References Cited

U.S. PATENT DOCUMENTS

| | | | |
|---|---|---|---|
| 4,165,747 A * | 8/1979 | Bermant | A61B 17/11 606/148 |
| 4,245,638 A | 1/1981 | Lebeck et al. | |
| 4,470,415 A | 9/1984 | Wozniak | |
| 4,553,543 A | 11/1985 | Amarasinghe | |
| 4,635,636 A * | 1/1987 | Goldstein | A61B 17/11 24/507 |
| 6,458,285 B1 | 10/2002 | Lyanna et al. | |
| 8,197,499 B2 | 6/2012 | Gurtner et al. | |
| 2015/0190134 A1* | 7/2015 | Weisshaupt | A61B 17/11 606/41 |

FOREIGN PATENT DOCUMENTS

| | | |
|---|---|---|
| WO | WO 00/42921 A1 | 7/2000 |
| WO | WO 2004/060142 A2 | 7/2004 |

\* cited by examiner

FIXING DEVICE FOR BLOOD VESSEL SUTURING

This application claims the benefit of Taiwan application Serial No. 107143900, filed Dec. 6, 2018, the disclosure of which is incorporated by reference herein in its entirety.

TECHNICAL FIELD

The disclosure relates in general to a surgical aid device, and more particularly to a fixing device for suturing of blood vessels.

BACKGROUND

End-to-end anastomosis of blood vessels, especially when suturing capillary vessels of 2 mm in diameter, relies heavily on the skill of the operator. Current suture assist device primarily performs end-to-end anastomosis of blood vessels by using commercially available vascular clips and ring-shaped anastomotic couplers. When the blood vessel is damaged, it is easy to cause the blood vessel to collapse, and the alignment is not easy when suturing the blood vessels. Since the anastomosis needle is easy to cause the blood vessel tear, the vascular clips are not easy to align, the vascular clips cannot be adjusted, and the positions of the blood vessels at each incision end are not fixed, so that the inner walls of the blood vessels are not easy to align during the suturing process, and it is easy to cause an increase in thrombus, so that the recovery of the patient after suturing is not good. When the current suture assist device performs suturing of blood vessels, the ends of the blood vessels are easily slipped and the inner walls of the blood vessels cannot be everted outwardly, such that there are many disadvantages in application, and it takes a long time to perform suturing of the blood vessels.

Therefore, how to more effectively assist the surgeon in performing vascular suture surgery to improve the accuracy of vascular suture and reduce the time spent on vascular suture is extremely important.

SUMMARY

The disclosure is directed to a fixing device for suturing of blood vessels, which is effective for assisting a surgeon in performing a vascular suture surgery.

According to one embodiment, a fixing device for suturing of blood vessels is provided, which comprises a connecting rod, a first clamping member, a second clamping member, a first extension tube and a second extension tube. One end of the first clamping member is disposed on the connecting rod, and the other end of the first clamping member has a first clamping head. One end of the second clamping member is disposed on the connecting rod, and the other end of the second clamping member has a second clamping head. The first extension tube is disposed on an inner side of the first clamping head. The second extension tube is disposed on an inner side of the second clamping head and opposite to the first extension tube, wherein a relative position of the first extension tube and the second extension tube is adjustable.

The above and other aspects of the disclosure will become better understood with regard to the following detailed description of the preferred but non-limiting embodiment(s). The following description is made with reference to the accompanying drawings.

DETAILED DESCRIPTION

Detailed descriptions of the disclosure are disclosed below with a number of embodiments. However, the disclosed embodiments are for explanatory and exemplary purposes only, not for limiting the scope of protection of the disclosure. Similar/identical designations are used to indicate similar/identical elements. Directional terms such as above, under, left, right, front or back are used in the following embodiments to indicate the directions of the accompanying drawings, not for limiting the disclosure.

According to an embodiment of the disclosure, a fixing device for suturing of blood vessels is provided to assist a surgeon in performing a vascular suturing surgery. The fixing device of the embodiment can be opened by the surgeon with a forceful flat-nose pliers, or can be closed by releasing an external force from the fixing device. The fixing device can perform clamping and hemostasis on two ends of the blood vessels by using two clamping members during the surgery operation, positioning and aligning the positions of the incisions at the ends of the two blood vessels, bringing the inner walls of the two blood vessels closer to each other when the two blood vessels are turned over, and suturing the inner walls of the two blood vessels with a suture line or a staple to complete the vascular suturing surgery. The components of the fixing device are described in detail below, but the disclosure is not limited to the drawings shown in the following embodiments.

Figure 1A:
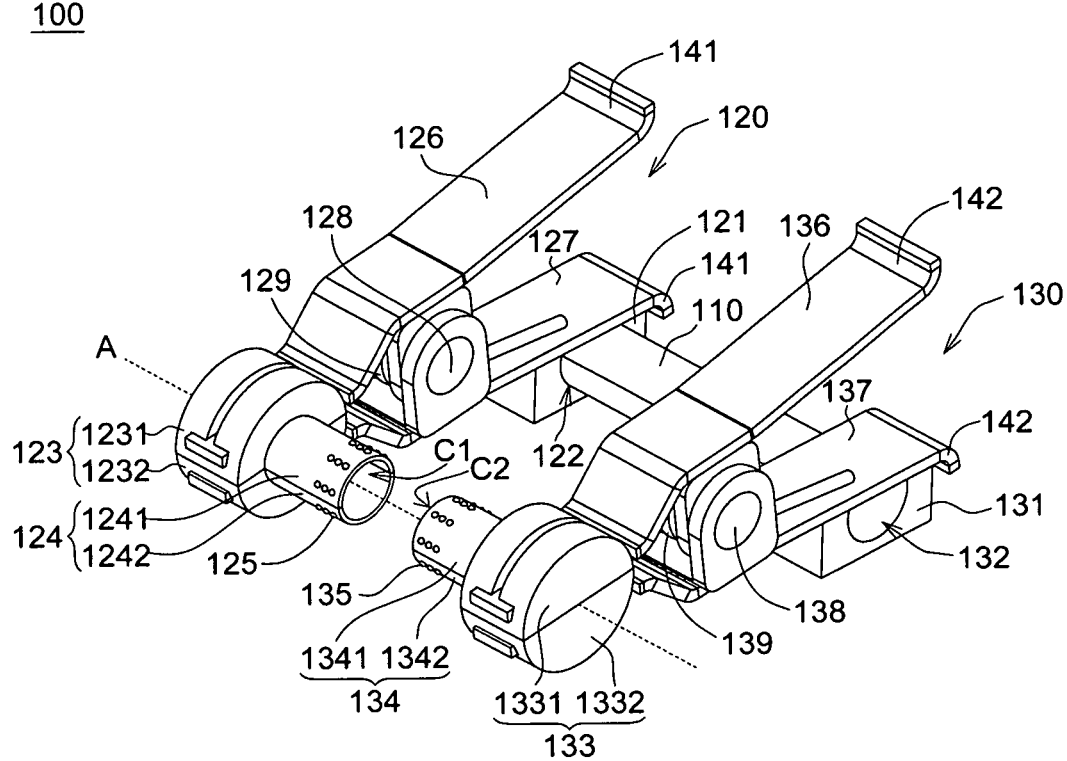
FIG. 1A is a schematic view showing a fixing device for suturing of blood vessels in a closed state according to an embodiment of the disclosure.
Figure 1B:
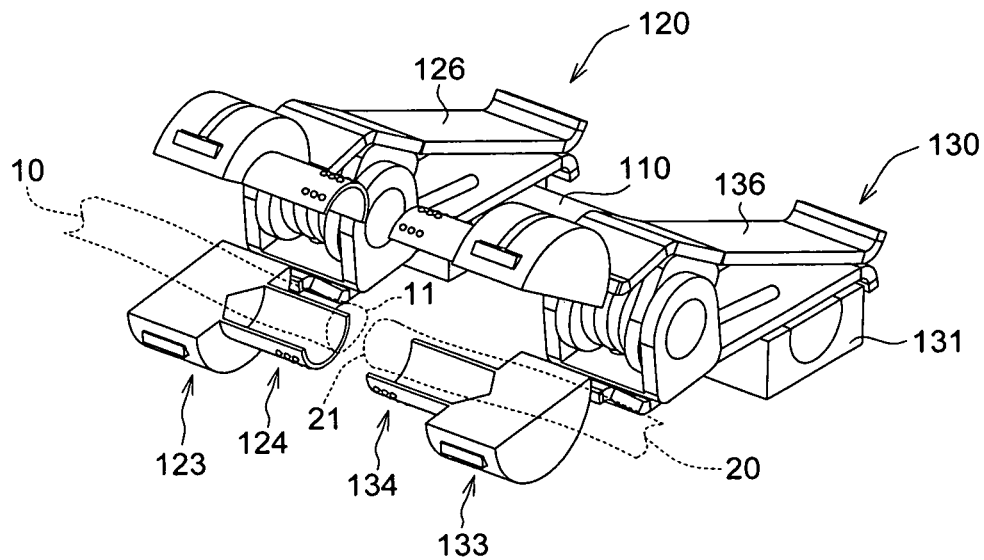
FIG. 1B is a schematic view showing a fixing device for suturing of blood vessels in an open state according to an embodiment of the disclosure.

Referring to FIGS. 1A and 1B, according to an embodiment of the disclosure, a fixing device 100 for suturing of blood vessels includes a connecting rod 110, a first clamping member 120, a second clamping member 130, a first extension tube 124 and a second extension tube 134.

The first clamping member 120 and the second clamping member 130 are respectively disposed on the connecting rod 110. The connecting rod 110 may be elongated, and the length of the connecting rod 110 is at least greater than or equal to the sum of the width of the first clamping member 120, the width of the second clamping member 130, and the shortest distance between the first clamping member 120 and the second clamping member 130. In an embodiment, the width of the first clamping member 120 is, for example, 4 mm, the width of the second clamping member 130 is, for example, 4 mm, and the shortest distance between the first clamping member 120 and the second clamping member 130 is, for example, 6 mm. The length of the connecting rod 110 is at least greater than or equal to 14 mm.

The first clamping member 120 and the second clamping member 130 are movably disposed on the connecting rod 110 such that the distance between the first clamping member 120 and the second clamping member 130 is adjustable. Specifically, the first clamping member 120 has a first fixing seat 121 at one end thereof, and the first fixing seat 121 has a first opening 122 for the connecting rod 110 to pass through the first opening 122. The second clamping member 130 has a second fixing seat 131 at one end thereof, and the second fixing seat 131 has a second opening 132 for the connecting rod 110 to pass through the second opening 132.

In an embodiment, the shapes of the first opening 122 and the second opening 132 are, for example, semicircular, square, rectangular, polygonal or other shapes except a circular shape, and a cross-sectional shape of the connecting rod 110 is, for example, semicircular, square, rectangular, polygonal or other cross-sectional shapes except a circular cross-sectional shape, such that the connecting rod 110 matches the shapes of the first opening 122 and the second opening 132. Therefore, the first clamping member 120 and the second clamping member 130 can slide on the connecting rod 110 and do not rotate relative to the connecting rod 110.

In an embodiment, the first clamping member 120 and the second clamping member 130 may also be designed such that one of the clamping members is slidable, and the other clamping member is non-slidable, so that only one of the clamping members is adjusted.

In addition, in an embodiment, the opposite sides of the connecting rod 110 are provided with two sealing kits (not shown), for example, when the first clamping member 120 and the second clamping member 130 are sleeved on the connecting rod 110, the two sealing kits can prevent the first clamping member 120 and the second clamping member 130 from sliding out of the connecting rod 110.

Referring to FIGS. 1A and 1B, the first clamping member 120 has a first clamping head 123 and a first extension tube 124 disposed on the inner side of the first clamping head 123. The second clamping member 130 has a second clamping head 133 and a second extension tube 134 disposed on the inner side of the second clamping head 133. The first extension tube 124 and the second extension tube 134 are opposed to each other on an axis A such that the axes of the first extension tube 124 and the second extension tube 134 are aligned with each other.

The relative position of the first extension tube 124 and the second extension tube 134 can be adjusted. That is, the distance between the first extension tube 124 and the second extension tube 134 can be adjusted. In particular, after clamping and aligning the two ends 11, 21 of the blood vessels, the two inner walls 12, 22 of the blood vessels everted at the two ends 11, 21 of the blood vessels are brought close to each other (see FIG. 3C) to facilitate the inner walls 12, 22 of the two blood vessels for stitching or stapling (see FIG. 3D). The length of the first extension tube 124 is, for example, 3-5 mm, and the length of the second extension tube 134 is, for example, 3-5 mm.

Figure 3A:
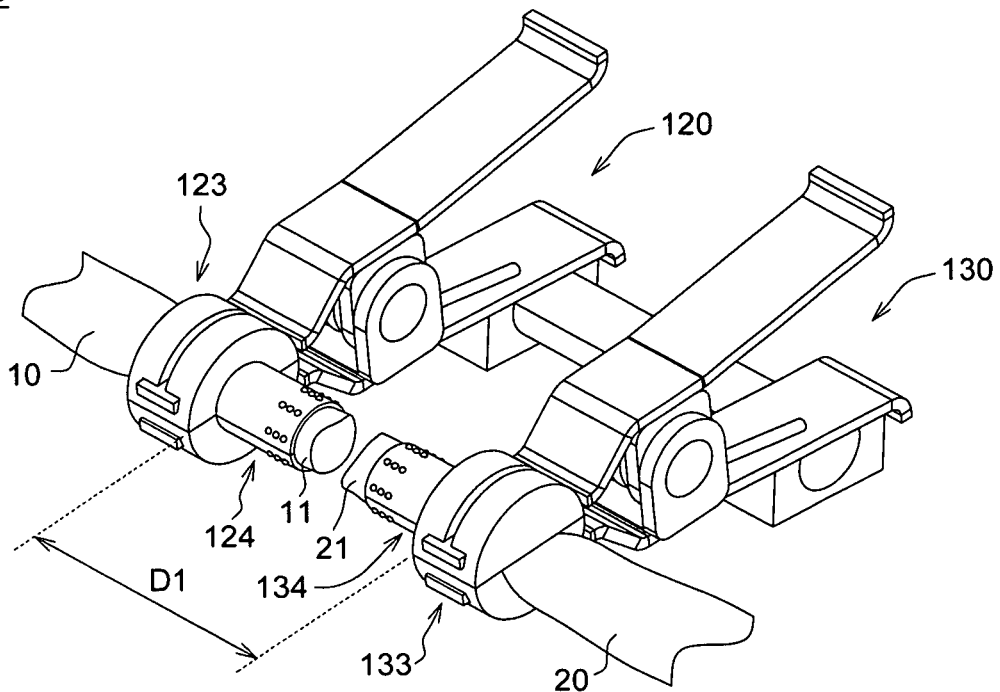
FIGS. 3A to 3D are schematic views respectively showing the use of the fixing device of the present embodiment to fix blood vessels for performing a vascular suture surgery.
Figure 3B:
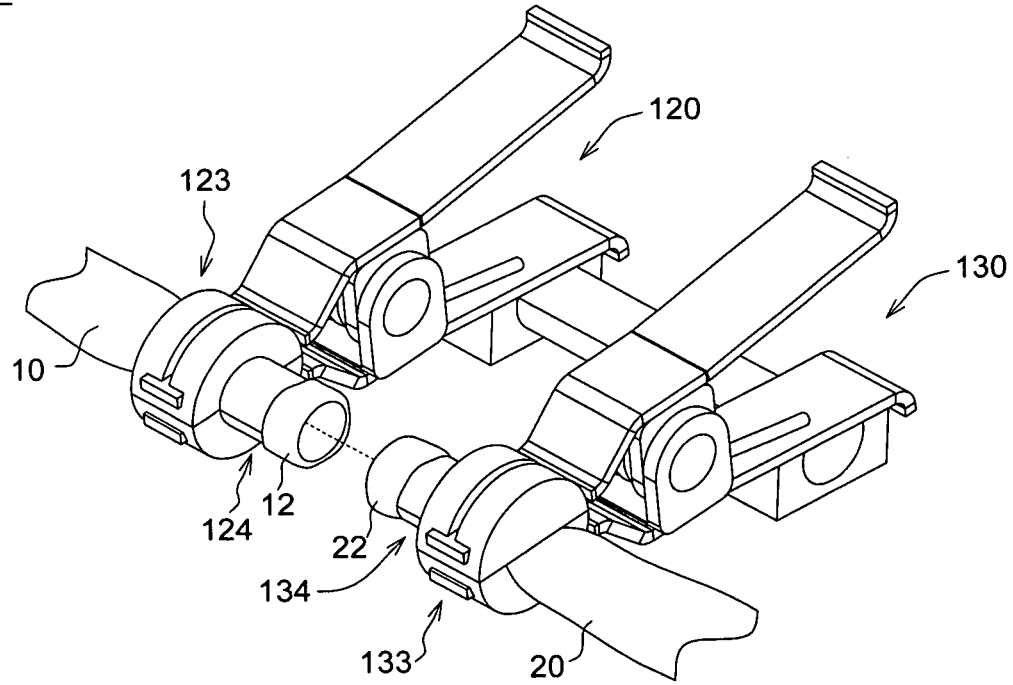

In the present embodiment, the first extension tube 124 has two oppositely-joined hollow tubes 1241, 1242, such as two semi-circular hollow tubes 1241, 1242, to form a first accommodation portion C1 for accommodating an end 11 of the blood vessel, and an exposed portion of the end 11 of the blood vessel can also be clamped and twisted via a clamper to bring the exposed portion of the inner wall 12 of the blood vessel being everted and cover the outer surface of the first extension tube 124 (see FIGS. 3A and 3B). In addition, the second extension tube 134 has two oppositely-joined hollow tubes 1341, 1342, such as two semi-circular hollow tubes 1341, 1342, to form a second accommodation portion C2 for accommodating another end 21 of the blood vessel, and an exposed portion of the end 21 of the blood vessel can also be clamped and twisted via a clamper to bring the exposed portion of the inner wall 22 of the blood vessel being everted and cover the outer surface of the second extension tube 134 (see FIGS. 3A and 3B). In one embodiment, the inner diameters of the hollow tubes 1241, 1242, 1341, 1342 is, for example, 3 mm, and the wall thicknesses of the hollow tubes 1241, 1242, 1341, 1342 is, for example, 0.15 mm.

On the other hand, the first clamping head 123 has two oppositely-joined solid tubes 1231, 1232, such as two semi-circular solid tubes 1231, 1232 for clamping the blood vessel 10 to make the blood vessel 10 be flattened so as to achieve hemostasis and positioning. In addition, the second clamping head 133 has two oppositely-joined solid tubes 1331, 1332, such as two semi-circular solid tubes 1331, 1332 for clamping another blood vessel 20, so that the another blood vessel 20 is flatten to achieve hemostasis and positioning. In one embodiment, the outer diameters of the solid tubes 1231, 1232, 1331, 1332 are, for example, 5 mm, and the axial widths of the solid tubes 1231, 1232, 1331, 1332 are, for example, 2.5 mm.

Figure 3C:
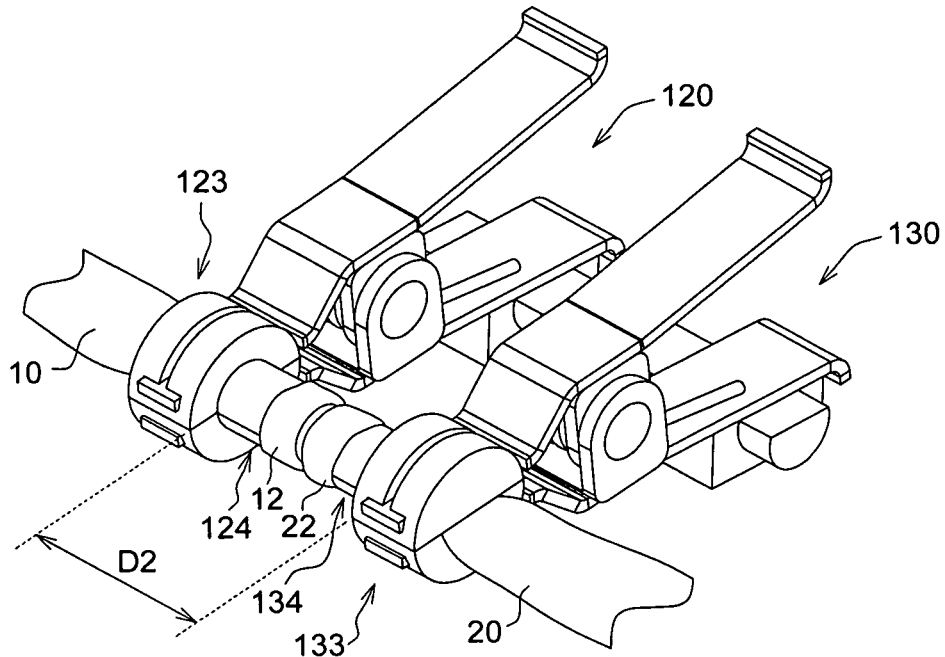
Figure 3D:
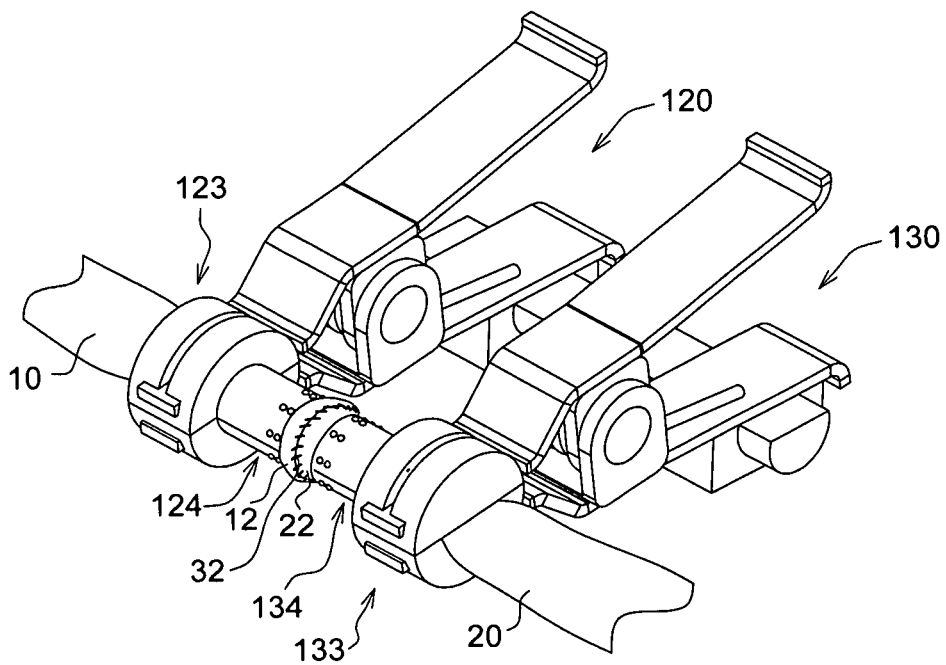

In the present embodiment, after the two ends 11, 21 of the blood vessels are positioned by the clamping heads and aligned with the axis A of the extension tube (as shown in FIG. 3A), the two inner walls 12, 22 of the blood vessels can be everted to cover the outer surface of the extension tube (as shown in FIG. 3B), and then bringing the two everted inner walls 12, 22 of the blood vessels closer to each other (as shown in FIG. 3C), and then using suture lines or staples for suturing or stapling of the two everted inner walls 12, 22 of the blood vessels (as shown in FIG. 3D) to complete the vascular suturing surgery.

Figure 1C:
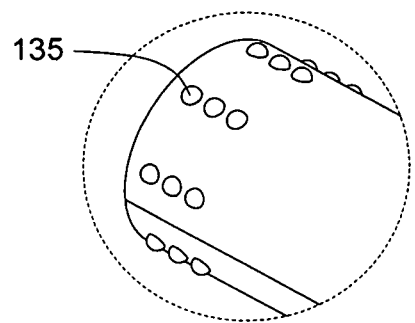
FIG. 1C is a schematic view showing anti-slip structure on the outer surface of the hollow tube according to an embodiment of the disclosure.
Figure 1D:
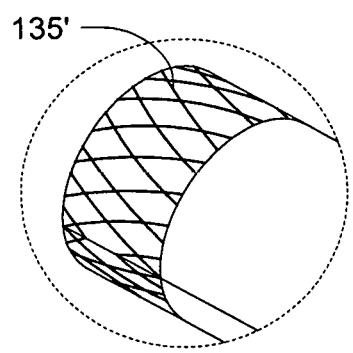
FIG. 1D is a schematic view showing another anti-slip structure on the outer surface of the hollow tube according to an embodiment of the disclosure.

The outer surface of the hollow tubes 1241, 1242 has, for example, an anti-slip structure 125 or 135', and the outer surface of the hollow tubes 1341, 1342 has, for example, an anti-slip structure 135 or 135'. Referring to FIGS. 1C and 1D, the anti-slip structure 135 or 135' may be a dot, a straight line pattern, a wave pattern, a mesh pattern or a combination thereof, and any surface convex structure capable of increasing friction may be used as the anti-slip structure. Further, the anti-slip structure 135 or 135' may be an anti-slip coating or a surface roughened coating to cause a roughened pattern on the outer surface of the hollow tubes 1241, 1242. In the present embodiment, the inwardly-everted outer walls of the two blood vessels can be rubbed against the anti-slip structure 135 or 135' without being easily stripped or slid, so as to facilitate the suturing or the two everted inner walls 12, 22 of the blood vessels by the stitch or the staple. In addition, the first extension tube 124 and the second extension tube 134 of the embodiment can be used as a supporting surface for the stapler to apply a force so as to ensure stapling position accurately.

Figure 4:
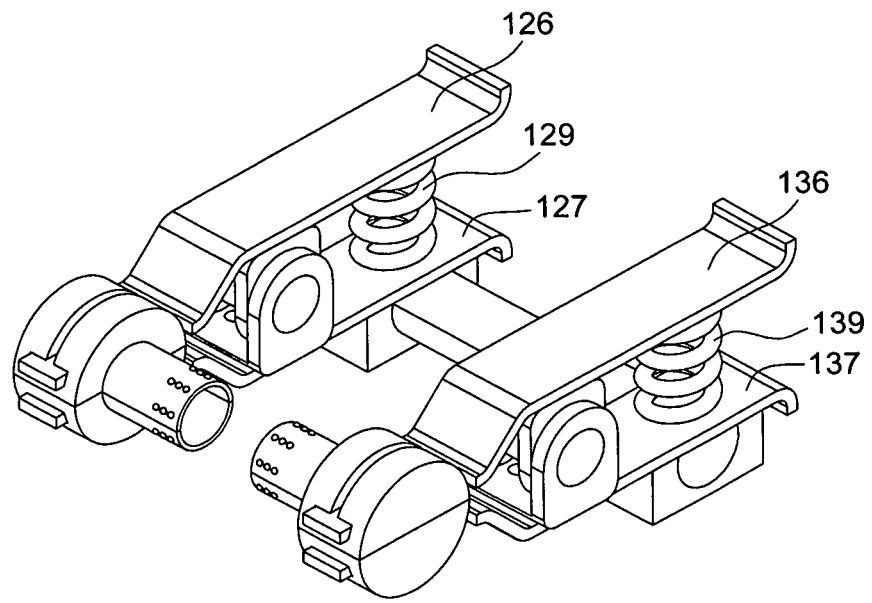
FIG. 4 is a schematic view of a fixing device for suturing of blood vessels according to another embodiment of the disclosure.
Figure 5:
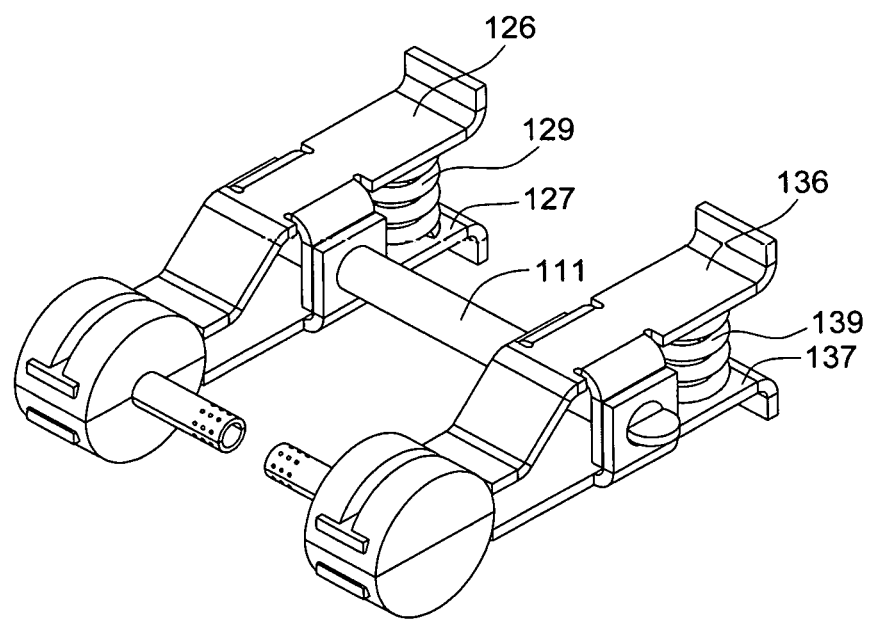
FIG. 5 is a schematic view showing a fixing device for suturing of blood vessels according to another embodiment of the disclosure.

Referring to FIGS. 1A and 1B, in an embodiment, the first clamping member 120 includes an upper clamping arm 126, a lower clamping arm 127, and a shaft portion 128. The upper clamping arm 126 and the lower clamping arm 127 are pivotally coupled to the shaft portion 128. In addition, the first clamping member 120 can further be provided with a spring 129 on the shaft portion 128 to form a clamping structure similar to a spring caliper. The lengths of the upper clamping arm 126 and the lower clamping arm 127 are, for example, 12-15 mm. Referring to FIG. 4, in another embodiment, the spring 129 may also be connected between the upper clamping arm 126 and the lower clamping arm 127 to form a clamping structure similar to a spring caliper, and the remaining components are illustrated in FIG. 1 and the symbols of the remaining components are no longer indicated. In addition, referring to FIG. 5, in another embodiment, the upper clamping arm 126 and the lower clamping arm 127 are openably and closably pivoted on a link 111 near the end of the clamping member. In addition to be the above-mentioned shaft portion 128, the link 111 can also be used as the connecting rod 110 in the FIG. 1A, so that the first clamping member 120 and the second clamping member 130 can slide on the link 111 respectively and do not rotate relative to the link 111.

Figure 6:
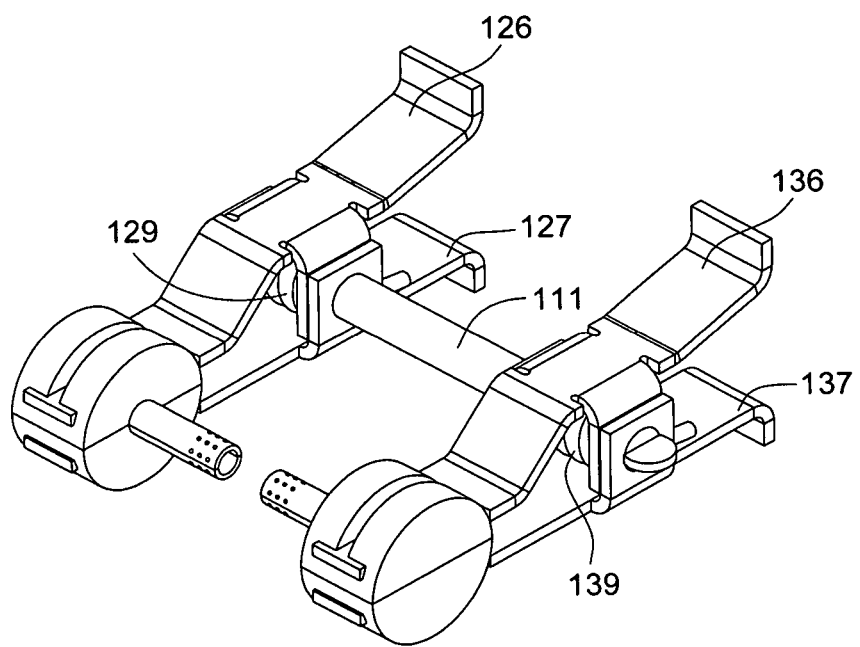
FIG. 6 is a schematic view of a fixing device for suturing of blood vessels according to another embodiment of the disclosure.

In the present embodiment, the user can simultaneously press the upper clamping arm 126 and the lower clamping arm 127 to rotate the upper clamping arm 126 relative to the lower clamping arm 127 to achieve the function of opening and closing. When the user simultaneously presses the upper clamping arm 126 and the lower clamping arm 127, the first clamping head 123 can be opened and the maximum opening height can be 5-7 mm, so that the blood vessel 11 can be placed in the first clamping head 123. Similarly, the second clamping member 130 can include an upper clamping arm 136, a lower clamping arm 137, a shaft portion 138, and a spring 139, which are similar to the structure of the first clamping member 120 and will not describe herein again. Referring to FIG. 4, a spring 139 may also be coupled between the upper clamping arm 136 and the lower clamping arm 137 to form a clamping structure similar to a spring caliper. In addition, referring to FIG. 5, the upper clamping arm 136 and the lower clamping arm 137 are openably and closably pivoted on the link 111 as described above. In addition, referring to FIG. 6, the springs 129, 139 may also be disposed on the link 111, as shown in FIG. 1A in which the springs 129, 139 are disposed on the shaft portion 128.

In addition, in order to facilitate pressing the upper clamping arm 126 and the lower clamping arm 127, the first clamping member 120 can further provide with two positioning grooves 141 on the outer surfaces of the upper clamping arm 126 and the lower clamping arm 127. The two positioning grooves 141 have, for example, curved surfaces, toothed surfaces or other types of surfaces that can be engaged with an object, and the user can use the flat-nose pliers (not shown) matched with the outer surfaces of the two positioning grooves 141 on the first clamping member 120 to increase the friction between the first clamping member 120 and the flat-nose pliers, thereby stably clamping the first clamping member 120. Similarly, the second clamping member 130 can also provide with two positioning grooves 142, which are similar to the structure of the first clamping member 120 and will not describe herein again.

According to an embodiment of the disclosure, another fixing device 101 for suturing of blood vessels is provided. The following description is only for the differences from the above embodiments, and the same/similar references denote the same/similar elements.

Figure 2A:
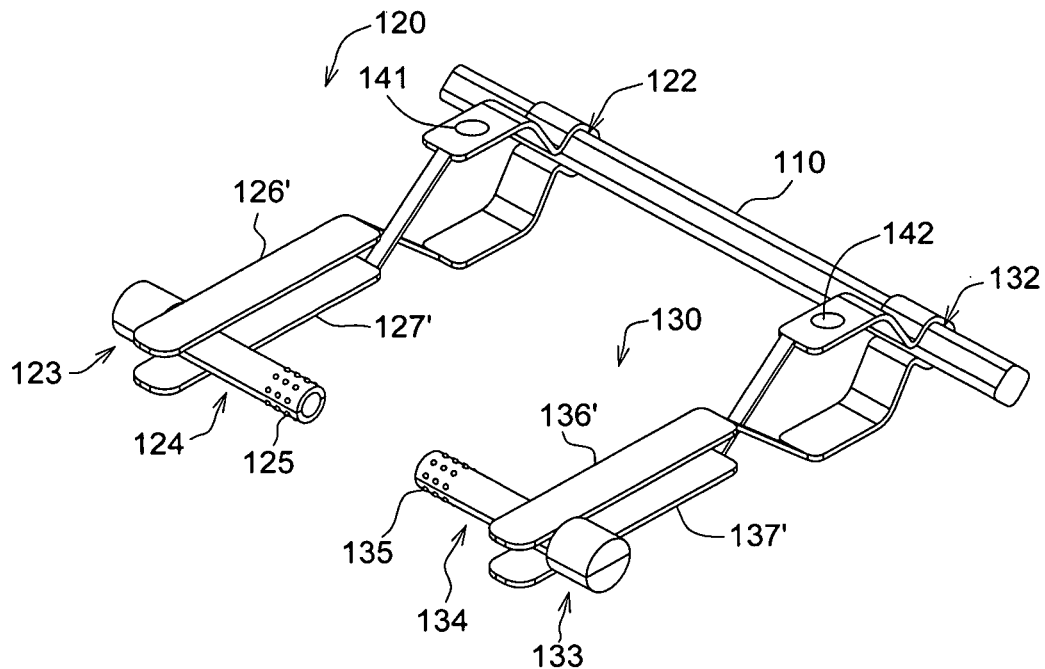
FIG. 2A is a schematic view showing a fixing device for suturing of blood vessels in a closed state according to another embodiment of the disclosure.
Figure 2B:
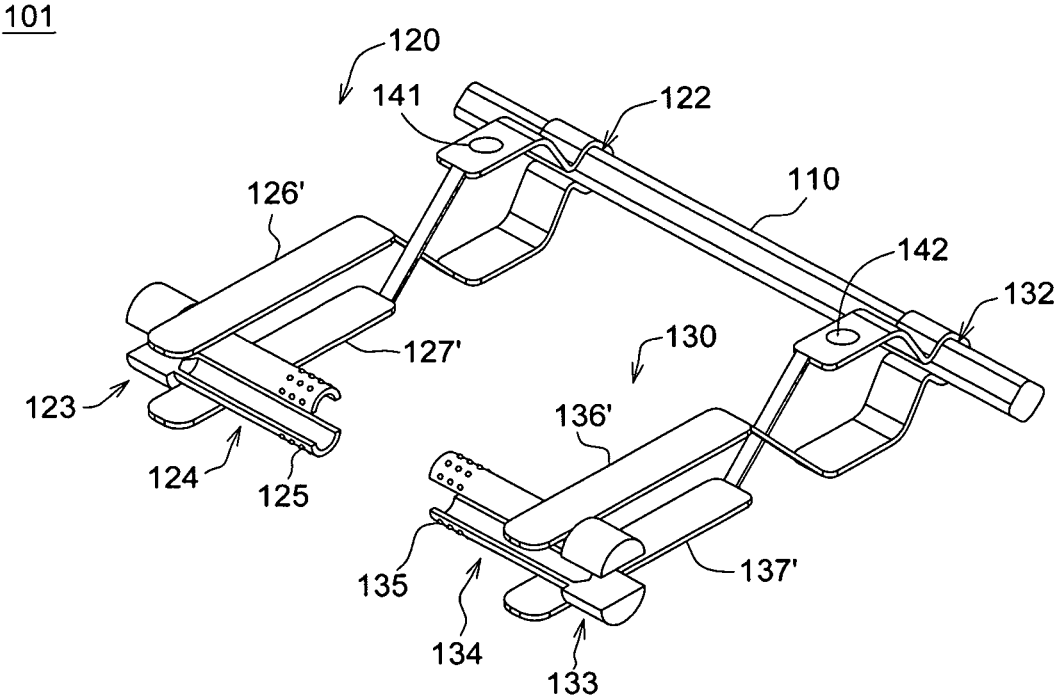
FIG. 2B is a schematic view showing the fixing device for suturing of blood vessels of FIG. 2A in an open state according to an embodiment of the disclosure.

Referring to FIGS. 2A and 2B, the fixing device 101 for suturing of blood vessels includes a connecting rod 110, a first clamping member 120, a second clamping member 130, a first extension tube 124, and a second extension tube 134. The difference from the above embodiment is that the first clamping member 120 includes two clamping arms 126' and 127', and the two clamping arms 126', 127' are integrally formed and intersect each other to form a first elastic clamping structure. The second clamping member 130 has two clamping arms 136', 137'. The two clamping arms 136', 137' are integrally formed and intersect each other to form a second elastic clamping structure. Therefore, the clamp members of the present embodiment do not need to be provided with the shaft portions 128, 138 of the above embodiment.

In addition, one end of the first clamping member 120 has a first opening 122, and one end of the second clamping member 130 has a second opening 132. The shape of the opening may be non-circular such as semicircular, square, rectangular, polygonal, etc. The connecting rod 110 is matched with the shape of the opening to enable the connecting rod 110 to pass through the respective openings of the first clamping member 120 and the second clamping member 130.

In the present embodiment, the first extension tube 124 and the second extension tube 134 respectively have two oppositely-joined hollow tubes, and the first clamping head 123 and the second clamping head 133 respectively have two oppositely-joined solid tubes. Furthermore, the outer surface of the hollow tubular body has, for example, an anti-slip structure 125, 135. In addition, the first clamping member 120 and the second clamping member 130 are respectively provided with two positioning grooves 141, 142, respectively. The foregoing has been described in detail in the above embodiments, and the functions thereof are the same, and will not describe herein again.

Referring to FIGS. 3A to 3D, which are schematic views showing the use of the fixing device 100 of the present embodiment to fix blood vessels for performing a vascular suturing surgery. In FIG. 3A, the distance between the first clamping member 120 and the second clamping member 130 is separated by a first distance D1, for example, 10-12 mm. The blood vessel 10 is clamped and positioned by the first clamping member 120, the second blood vessel 20 is clamped and positioned by the second clamping member 130, and the two ends 11, 21 of the blood vessels are aligned with each other on the axis. In FIG. 3B, a portion of the inner wall 12 of the blood vessel is everted to cover the outer surface of the first extension tube 124, and a portion of the inner wall 22 of the blood vessel is everted to cover the outer surface of the second extension tube 134. In FIG. 3C, the distance between the first clamping member 120 and the second clamping member 130 is adjusted to be a second distance D2 (less than the first distance D1), for example, 6-8 mm, so that the inner walls 12, 22 of the two ends 11, 21 of the blood vessels are closer to each other. Next, in FIG. 3C, the everted inner walls 12, 22 of the two blood vessels are sutured or stapled with the suture lines 32 or staples to complete the vascular suturing surgery.

The fixing device for suturing of blood vessels disclosed in the above embodiments of the disclosure uses the two extension tubes to support the blood vessels to avoid the disadvantage that the blood vessels collapses and the inner walls of the blood vessels are not easily everted outwardly, such that the alignment of the two ends of the blood vessels is accurate, and the blood stream can flow smoothly after suturing to reduce the chance of embolism, and the suturing time can be reduced to 10 minutes, thereby effectively assisting the surgeon in performing the vascular suturing surgery. In addition to the foregoing disclosure for suturing of blood vessels, the fixing device can also be applied to suturing of tubular tissue, such as bile ducts, ureters, etc., to improve the accuracy of the suturing of the tubular tissue and to reduce the time spent on suturing of the tubular tissue.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A fixing device for suturing of blood vessels, comprising:
   a connecting rod;
   a first clamping member, wherein one end of the first clamping member is disposed on the connecting rod, and the first clamping member has a first clamping head;
   a second clamping member, wherein one end of the second clamping member is disposed on the connecting rod, and the second clamping member has a second clamping head, wherein the first clamping head and the second clamping head respectively comprise two oppositely-joined solid tubes;
   a first extension tube disposed on an inner side of the first clamping head; and
   a second extension tube is disposed on an inner side of the second clamping head and opposite to the first extension tube, wherein a relative position of the first extension tube and the second extension tube is adjustable.

2. The fixing device according to claim 1, wherein the first clamping member and the second clamping member respectively comprise two clamping arms and a shaft portion, and the two clamping arms are openably and closably pivoted on the shaft portion.

3. The fixing device according to claim 2, wherein the first clamping member and the second clamping member respectively comprise a spring disposed on the shaft portion or connected between the two clamping arms.

4. The fixing device according to claim 1, wherein the first clamping member and the second clamping member respectively comprise two clamping arms, and the two clamping arms are openably and closably pivoted on the connecting rod.

5. The fixing device according to claim 4, wherein the first clamping member and the second clamping member respectively comprise a spring disposed on the connecting rod or connected between the two clamping arms.

6. The fixing device according to claim 2, wherein outer surfaces of the two clamping arms are respectively provided with a positioning groove.

7. The fixing device according to claim 4, wherein outer surfaces of the two clamping arms are respectively provided with a positioning groove.

8. The fixing device according to claim 1, wherein the first extension tube and the second extension tube respectively comprise two oppositely-joined hollow tubes.

9. The fixing device according to claim 8, wherein outer surfaces of the two oppositely-joined hollow tubes respectively have an anti-slip structure.

10. The fixing device according to claim 9, wherein the anti-slip structure is a dot, a straight line pattern, a wave pattern, a mesh pattern, or a combination thereof.

11. The fixing device according to claim 1, wherein the first clamping member and the second clamping member respectively have a fixing seat, each of the fixing seats has an opening, and the connecting rod passes through the openings of the first clamping member and the second clamping member.

12. The fixing device according to claim 11, wherein the opening has a non-circular shape, and the connecting rod matches the shape of the opening.

13. The fixing device according to claim 1, wherein the first clamping member and the second clamping member respectively comprise two clamping arms, the two clamping arms of the first clamping member are integrally formed and intersect with each other to form a first elastic clamping structure and the two clamping arms of the second clamping member are integrally formed and intersect with each other to form a second elastic clamping structure.

14. The fixing device according to claim 13, wherein outer surfaces of the two clamping arms are respectively provided with a positioning groove.

* * * * *